US008921322B2

(12) United States Patent
Favre et al.

(10) Patent No.: US 8,921,322 B2
(45) Date of Patent: Dec. 30, 2014

(54) USE OF AT LEAST ONE BOTULINUM NEUROTOXIN FOR TREATING THE PAIN INDUCED BY THERAPEUTIC TREATMENTS FOR THE AIDS VIRUS

(75) Inventors: Christine Favre, Saint Maurice Montcouronne (FR); Michel Auguet, Palaiseau (FR); Pierre-Etienne Chabrier De Lassauniere, Paris (FR)

(73) Assignee: Ipsen Pharma S.A.S., Boulogne Billancourt (FR)

( * ) Notice: Subject to any disclaimer, the term of this patent is extended or adjusted under 35 U.S.C. 154(b) by 0 days.

(21) Appl. No.: 12/520,610

(22) PCT Filed: Dec. 17, 2007

(86) PCT No.: PCT/FR2007/002091
§ 371 (c)(1),
(2), (4) Date: Jun. 22, 2009

(87) PCT Pub. No.: WO2008/090287
PCT Pub. Date: Jul. 31, 2008

(65) Prior Publication Data
US 2010/0029566 A1    Feb. 4, 2010

(30) Foreign Application Priority Data

Dec. 22, 2006    (FR) ..................................... 06 11244

(51) Int. Cl.
| | | |
|---|---|---|
| *A61K 38/00* | (2006.01) | |
| *A61P 25/02* | (2006.01) | |
| *A61P 23/00* | (2006.01) | |
| *A61K 39/00* | (2006.01) | |
| *A61K 39/38* | (2006.01) | |
| *A61K 39/21* | (2006.01) | |
| *A61K 39/08* | (2006.01) | |
| *A61K 38/48* | (2006.01) | |

(52) U.S. Cl.
CPC .................................. *A61K 38/4893* (2013.01)
USPC ... 514/18.2; 514/18.3; 424/188.1; 424/184.1; 424/247.1

(58) Field of Classification Search
CPC ... A61K 38/4893; A61K 9/0019; C07K 14/33
See application file for complete search history.

(56) References Cited

U.S. PATENT DOCUMENTS

| | | |
|---|---|---|
| 4,457,916 A | 7/1984 | Hayashi et al. |
| 6,136,551 A | 10/2000 | Aoki et al. |
| 6,368,605 B1 | 4/2002 | Donovan |
| 7,704,524 B2 | 4/2010 | Donovan |
| 8,273,359 B2 | 9/2012 | Favre |
| 8,784,841 B2 | 7/2014 | Favre et al. |
| 2002/0064536 A1 | 5/2002 | Hunt |
| 2002/0192239 A1 | 12/2002 | Borodic et al. |
| 2003/0138437 A1 | 7/2003 | Hunt |
| 2004/0247623 A1 | 12/2004 | Cady |
| 2005/0147625 A1 | 7/2005 | First |
| 2005/0152905 A1 | 7/2005 | Omoigui |
| 2006/0178354 A1 | 8/2006 | Lucas |
| 2006/0240043 A1 | 10/2006 | Meyerson et al. |
| 2006/0269575 A1 * | 11/2006 | Hunt ......................... 424/239.1 |
| 2008/0232851 A1 | 9/2008 | Park et al. |
| 2009/0028908 A1 * | 1/2009 | Donovan .................... 424/239.1 |
| 2009/0214466 A1 | 8/2009 | Levin |
| 2009/0232849 A1 | 9/2009 | Gallez et al. |
| 2009/0232851 A1 | 9/2009 | Auguet et al. |
| 2010/0029566 A1 | 2/2010 | Favre et al. |
| 2010/0068231 A1 | 3/2010 | Favre et al. |
| 2011/0038893 A1 | 2/2011 | Favre et al. |
| 2011/0152198 A1 * | 6/2011 | Hunt ........................... 514/18.8 |

FOREIGN PATENT DOCUMENTS

| | | |
|---|---|---|
| AU | 2007259122 | 11/2012 |
| CA | 2 586 181 | 5/2006 |
| EP | 1 604 681 | 4/2005 |
| EP | 1 604 681 | 12/2005 |
| EP | 2 037 956 | 2/2014 |
| GB | 2419526 A * | 3/2005 |
| GB | 2 416 692 | 2/2006 |
| GB | 2 419 526 | 3/2006 |
| KR | 2003018827 | 3/2003 |
| WO | WO 95/17904 | 7/1995 |
| WO | 01/26736 | 4/2001 |
| WO | WO 01/26736 | 4/2001 |
| WO | WO 01/47512 | 7/2001 |
| WO | 01/58472 | 8/2001 |
| WO | WO 01/58472 | 8/2001 |
| WO | WO 01/76576 | 10/2001 |
| WO | WO 01/78760 | 10/2001 |
| WO | WO 2004/006954 | 1/2004 |
| WO | WO 2004/075832 | 9/2004 |
| WO | 2005/082339 | 9/2005 |
| WO | WO 2005/082339 | 9/2005 |
| WO | 2006/005910 | 1/2006 |

(Continued)

OTHER PUBLICATIONS

Klein et al (Dematol. Surg, 30:3:Mar. 2004).*

(Continued)

*Primary Examiner* — Gary Nickol
*Assistant Examiner* — Lakia Tongue
(74) *Attorney, Agent, or Firm* — Hunton & Williams LLP

(57) ABSTRACT

The present invention relates to the use of at least one botulinum neurotoxin for the production of a medicament for treating or preventing pain induced by a medicament used for treating the AIDS virus.

15 Claims, No Drawings

(56) References Cited

FOREIGN PATENT DOCUMENTS

| WO | WO 2006/005912 | 1/2006 |
|----|----------------|--------|
| WO | WO 2006/042249 | 4/2006 |
| WO | WO 2006/049248 | 5/2006 |
| WO | WO 2007/144493 | 12/2007 |

OTHER PUBLICATIONS

Keswani et al (AIDS 2002, 16:2105-2117).*
Dieleman et al (Archives of Internal Medicine, vol. 162, No. 13, Jul. 8, 2002, p. 1492-1501).*
Klein et al., Dematol. Surg, 2004; 30: 452-455.*
Gonzalez-Duarte et al., The PRN Notebook, 2006; 11(2): 24-29.*
Argoff, The Clinical Journal of Pain, 2002; 18: S177-S181.*
Calabrese et al., Expert Opinion on Investigational Drugs, 1998; 7(12): 2043-2060.*
Jabbari et al., Pain Medicine, 2003; 4(2): 206-210.*
Bach-Rojecky et al., "Botulinum Toxin Type A in Experimental Neuropathic Pain," Journal of Neural Transmission, vol. 112, No. 2, pp. 215-219 (2005).
Frich et al., "Pain and Pain Treatment in AIDS Patients: A Longitudinal Study," Journal of Pain and Symptom Management, vol. 19, No. 5, pp. 339-347 (2000).
Joseph et al., "Novel Mechanism of Enhanced Nociception in a Model of AIDS Therapy-Induced Painful Peripheral Neuropathy in the Rat," Pain, vol. 107, pp. 147-158 (2004).
Keswani et al., "HIV-Associated Sensory Neuropathies," AIDS, vol. 16, pp. 2105-2117 (2002).
Klein, "The Therapeutic Potential of Botulinum Toxin," Publication for American Society for Dermatologic Surgery, vol. 30, No. 3, pp. 452-455 (2004).
Liu et al., "Botulinum Toxin A Relieved Neuropathic Pain in a Case of Post-Herpetic Neuralgia," Pain Medicine, vol. 7, No. 1, pp. 89-91 (2006).
Luciano et al., "Recent Developments in the HIV Neuropathies," Current Opinion in Neurology, vol. 16, pp. 403-409 (2003).
Noguera et al., "Botulinum Toxin in the Treatment of Spasticity in HIV-Infected Children Affected with Progressive Encephalopathy," AIDS, vol. 18, No. 2, pp. 352-353 (2004).
International Search Report for International Application No. PCT/FR2007/002091 mailed Jul. 29, 2008.
Dougherty et al., (2004) Pain 109:132-142.
Ansiaux, et al. (2007) *Expert Opinion on Investigational Drugs*. 16(2): 209-218.
Aoki (2005) *NeuroToxicology*. 26(5): 785-793.
Argoff, et al. (2002) *The Journal of Clinical Pain*. 18: S177-S181.
Attal, et al. (2008) *Neurology*. 70(11): A167, P03.168.
Auguet, et al. (2008) *Toxicon*. 51(Suppl. 1): 9, Abstract #24.
Bach-Rojecky, et al. (2005) *Basic Science—Croatian Medical Journal*. 46(2): 201-208.
Bueschen (1990) *Clinical Methods: The History, Physical, and Laboratory Examinations* [3rd Ed.] Chapter 182 "Flank Pain", pp. 845-846.
Cata, et al. (2008) *Brain Research* 1229: 100-110.
Cui, et al. (2004) *Pain*. 107: 125-133.
Farve-Guilmard, et al. (2009) *European Journal of Pharmacology*. 617: 48-53.
Favre-Guilmard, et al. (2008) *Toxicon*. 51(Supp. 1): 10.
Guokai, et al. (2003) *Chinese Journal of Anesthesiology*. 23(2): 157-159.
Jabbari, et al. (2003) *Pain Medicine*. 4(2): 206-210.
Jacobson, et al. (2008) *Applied and Environmental Microbiology*. 74(9): 2778-2786.
Kern, et al. (Apr. 2004) *Nervenarzt*. 75(4), Not translated.
Ledeboer, et al. (2007) *Brain, Behavior and Immunity*. 21: 686-698.
Lo Nigro, et al. (2002) *Medical and Pediatric Oncology*. 38(2): 150.
Luvisetto, et al. (2006) *Brain Research—Research Report*. 1082(1): 124-31.
Luvisetto, et al. (2007) *NeuroScience*. 145: 1-4.
Park, et al. (2006) *Canadian Journal of Anesthesia*. 53(5): 470-477.
Polomano, et al. (2001) *Pain*. 94: 293-304.
Ranoux, et al. (2008) *Annals of Neurology*. 64(3): 274-283.
Voller, et al. (2003) *Neurology*. 61(7): 940-944.
Yuan, et al. (2009) *Neurology*. 72(17): 1473-1478.
Webb, et al. (2006) *Drug Metab Rev*. 38(1-2): 89-116.
The Merck Index: An Encyclopedia of Chemicals and Drugs, 9th Ed., Merck & Co. (1976) p. 814, "Morphine ".
Blersch, et al. (2002) *Journal of the Neurological Sciences*. 205m(1): 59-63.
Gordon & Love (Dec. 2004) *Pain Management Nursing* 5(4) [suppl 1]: 19-33.
NINDS Peripheral Neuropathy Information Page (2011), 3 pages total.
Park & Moon (2008) "Antinociceptive Effects of Botulinum Toxin A for the Treatment of Neuropathic Pain." *Reviews in Analgesia* 10(1): 1-9 [Abstract only].
International Search Report for International Application No. PCT/FR2007/000956, mailed on Feb. 22, 2008.
International Search Report for International Application No. PCT/IB2009/005750, mailed Jul. 10, 2009.
International Search Report for International Application No. PCT/FR2007/001773, mailed Apr. 28, 2008.
Sudaraj, et al. (2004) *Pain Practice* 4(3): 229-234.
Barwood, et al. (2000) *Developmental Medicine & Child Neurology* 42: 116-121.
Kern, et al. (2004) *J Rehabil Med* 36: 238-239.
AFSSAPS, Rapport Public d'Evaluation, Botox 50 Unites Allergan, poudre pour solution injectable, Botox 100 Unites Allergan, poudre pour solution injectable, Botox 200 Unites Allergan, poudre pour solution injectable (4 pages) a report published by National Security Agency of Medicines and Health Products of France (2011).
Gordon, et al. "Pharmacologic management of neuropathic pain." *Pain Management Nursing* (2004) 5: 19-33 [Abstract].
Hill "Phantom Limb Pain: A Review of the Literature on Attributes and Potential Mechanisms" *Journal of Pain and Symptom Management* (1999) 17(2): 125-142.
Kern, et al. "Long-term treatment of phantom and stump pain with type A botulinum toxin for 1 year. First clinical observations" *NERVENARZT* (2004) 75(4): 336-340 [Abstract].
Kidd & Urban "Mechanisms of Inflammatory Pain." *British Journal of Anaesthesia* (2001) 87(1): 3-11.
Khoromi, et al. "Morphine, Nortriptyline and their Combination vs. Placebo in Patients with Chronic Lumbar Root Pain" *Pain* (2007) 130(1-2): 66-75.
Radhakrishnan, et al. *Current Protocols in Pharmacology* (2004) 5.35.1-5.35.28.
Zane, et al. (2007) "Morphine Dosing in Acute Pain: How Much Is Enough?" *NEJM Journal Watch* (2 pages).
Zhang, et al. "Antiangiogenic Treatment with Three Thrombospondin-1 Type 1 Repeats versus Gemcitabine in an Orthotopic Human Pancreatic Cancer Model" Clin Cancer Res (2005) 11: 5622-5630.
Meyer (2008) SA Fam Pract 50(3): 40-49.
NINDS Peripheral Neuropathy Information Page (2011), http://www.ninds.nih.gov/disorders/peripheralneuropathy/detail_peripheralneuropathy.htm.
Tarantino (2002) Techniques in Regional Anesthesia and Pain Management 6(1): 33-38.
Khotomi, et al. *Pain* 2007 130(1): 66-75.
Zhang, et al. *Clin Cancer Res* 2005, 11: 5622-5630.

* cited by examiner

USE OF AT LEAST ONE BOTULINUM NEUROTOXIN FOR TREATING THE PAIN INDUCED BY THERAPEUTIC TREATMENTS FOR THE AIDS VIRUS

CROSS-REFERENCE TO RELATED APPLICATIONS

This application is the U.S. National Stage filing of International Application No. PCT/FR2007/002091, filed Dec. 17, 2007, the disclosure of which is hereby incorporated by reference as if fully set forth herein, which claims priority to FR-0611244, filed Dec. 22, 2006, the disclosure of which is hereby incorporated by reference as if fully set forth herein.

FIELD OF THE INVENTION

The object of the present invention is the use of at least one botulinum neurotoxin to obtain a medicament for treating or preventing pain induced by anti-HIV drugs.

BACKGROUND OF THE INVENTION

AIDS is a disorder that is still difficult to relieve and cure. Furthermore, the therapeutic treatments of AIDS currently available have the side effect of producing pain, and the pain induced includes nociceptive, neuropathic and idiopathic pain.

Several studies have been conducted in the use of botulinum toxin to attenuate or prevent various different disorders linked to HIV. These different uses of toxins have been described in the scientific and medical literature.

The use of botulinum toxin as an analgesic for the pain engendered by HIV itself is known from the scientific publication by Klein A. W. "The therapeutic potential of botulinum toxin", Dermatologic Surgery, vol 30, no. 3, March 2004, pages 452-455.

The botulinum toxin used in the context of treating children suffering from HIV and concomitantly suffering from spasmodic paralysis and cerebral paralysis linked to HIV is described in the scientific publication of Noguera et al. "Botulinum toxin in the treatment of spasticity in HIV-infected children affected with progressive encephalopathy", AIDS, vol. 18, no. 2, 2004, pages 352-353.

A study of the use of botulinum toxin in case of post-herpes neuralgia is described in the scientific publication of Liu HSU-TANG et al. "Botulinum toxin A relieved neuropathic pain in a case of post herpetic neuralgia" Pain Medicine, 2006, vol. 7, no. 1, Jan. 2006, pages 89-91.

The publication of Bach-Rojecky L et al. "Botulinum toxin type A in experimental neuropathic pain" Journal of Neural Transmission, vol. 112, no. 2, 1 Feb. 2005, pp. 215-219, reports the reduction of mechanical and thermal hyperalgesia as a result of using botulinum toxin in the particular context of an experiment carried out on rats, which had previously undergone partial transverse section of the sciatic nerve.

Amongst the most common types of pain in AIDS patients induced by anti-HIV drugs, abdominal pain, headaches, peripheral neuropathies, myalgia or arthralgia, can be mentioned, this list not being exhaustive.

Pain of these types affects many patients infected by HIV and chronically treated, for example for more than one year, by a chemical treatment to combat AIDS. Pain of this type should be distinguished from the pain induced by the virus itself. In fact, this pain is induced by the anti-HIV drug or drugs administered to the patients for the purpose of treating them.

The pain attributable to anti-HIV drugs has distinctive semiological characteristics. For example, peripheral neuropathy is characterized by continuous, diffuse pain with no mechanical or inflammatory rhythm and of a burning nature. Against this background of continuous pain other symptoms can occur, attacks of spontaneous pain such as stabbing or tingling pain and more particularly tingling in the extremities of members, or electrical discharges. The topography of these symptoms corresponds to a distribution compatible with a peripheral or central systematization, In other terms the topography of this neuropathic pain attributable to the anti-HIV drugs is independent of the topography of infection by the virus.

Among the known treatments for this pain, for example the administration of anticonvulsants, anti-depressants or opiates such as morphine can also be mentioned.

However, the use of the compounds currently available that make it possible to reduce the pain induced by treatment with anti-HIV drugs is not satisfactory because it requires the use of high doses of drugs or frequent re-administration of the drug with the possible development of resistance to the drug or habituation. In addition, these analgesic treatments can induce side effects, which occur in addition to those already induced by AIDS or by the treatment for it.

The impact of the suffering induced often has a devastating effect on the quality of life of the people affected and so it has become necessary to find another way to treat or prevent the pain induced by the anti-HIV drugs.

Thus the problem that the invention intended to solve is to find a new treatment for pain induced by the anti-HIV treatments, in particular antiretroviral treatments.

DETAILED DESCRIPTION OF THE PREFERRED EMBODIMENTS

For this purpose, the present invention proposes to use at least one botulinum neurotoxin to obtain a drug for treating or preventing the pain induced by anti-HIV drugs.

The invention offers some decisive advantages, in particular that of avoiding or preventing pain following treatment with an anti-HIV drug, and so to make it possible to increase the doses of anti-HIV treatment without increasing pain.

Advantageously, the invention makes it possible to prevent or relieve the pain without interfering with the efficacy of the anti-HIV treatment.

Finally, the invention has the advantage of being able to be used in all industries, in particular the pharmaceutical and cosmetic industries.

Other advantages and characteristics of the invention will appear clearly from reading the description and examples, given non-restrictively and purely by way of illustration, that follow.

By "pain" should be understood in the meaning of the present invention "any unpleasant emotional or sensory experience associated with present or potential tissue damage, or described by the patient in such terms".

By the expression botulinum neurotoxin, is meant a botulinum toxin which is either a free protein (i.e. free of any protein that complexes it), or a protein complex, the said protein complex may include, for example, hemagglutinin (HA protein) associated with botulinum toxin, or a protein fragment.

By the expression "botulinum toxin", is meant a substance having the biological activity of botulinum toxin, which can for example be a protein, a polypeptide, a peptide, a fusion protein, a truncated protein, a chimeric protein, a mutant protein or a recombinant protein.

By the expression "biological activity of botulinum toxin", is meant in the sense of the present invention either muscular paralysis or inhibition of exocytosis, in particular of the exocytosis of acetylcholine or another neurotransmitter.

By protein, polypeptide or peptide is meant in the sense of the present invention, a polymer of amino acids, whether natural or not, whether levorotatory or not, or dextrorotatory or not.

By chimeric protein, is meant in the sense of the present invention a protein obtained after associating different types of substance, for instance, after combining lipids, glycolipids, peptides, polypeptides, proteins, glycoproteins, carbohydrates, polysaccharides, nucleic acids, polyethylene glycol, etc.

Botulinum toxin, in particular type A1 botulinum toxin (DYSPORT® marketed by Ipsen or BOTOX® marketed by Allergan), has been in use since the 1980s to treat various human diseases/disorders. Amongst the diseases/disorders that can be treated with botulinum toxin, we can mention amongst others muscular disorders (for example blepharospasm, or spasticity in adults or children, wry-neck, strabism), hyperhidrosis (or excessive perspiration), hypersalivation, or even glabellar lines.

Pure or virtually pure botulinum neurotoxin can be obtained from a protein complex containing botulinum toxin, for example according to the method described in Current topics in *Microbiology and Immunology* (1995), 195, p. 151-154. Pure or virtually pure botulinum neurotoxin can be obtained for instance by purifying a fermentation medium or culture broth containing a strain of *Clostridium botulinum*, and enriched, for example, with meat or proteinaceous nutrient.

The purpose of the present invention is firstly the use of a botulinum neurotoxin to obtain a medicament intended for treating or preventing pain induced by anti-HIV drugs.

Preferably, the present invention is not intended for the treatment of HIV, i.e. the virus itself, nor to treat or prevent the pain induced by the virus itself or the disease itself.

According to a variant, the object of the invention is the use of at least one botulinum neurotoxin to obtain a medicament for treating or preventing the pain induced by anti-HIV drugs, and not the pain induced by the HIV or the disease induced by the HIV.

Preferably, the use according to the invention of at least one botulinum neurotoxin to obtain a medicament that can be used to treat or prevent the pain induced by the anti-HIV drugs and administered to patients suffering from AIDS.

More preferably, the pain to be treated or prevented according to the invention is induced by anti-HIV drugs chosen from inhibitors of inverse transcriptase, antiproteases, fusion inhibitors, cytotoxics and interleukins.

Preferably, the anti-HIV drug(s) are chosen from the following compounds or mixtures of them:
zidovudin (AZT), didanosine, stavudin, zalcitabin, lamivudin, neviparin, abacadir, emtricitabin (for the inhibitors of inverse transferase);
saquinavir, ritonavir, indinavir, nelfinavir, amprenavir, tenofovir, atazanavir, a mixture of lopinavir, ritonavir and fosamprenavir (for the antiproteases);
enfuvirtide (for fusion inhibitors);
IL2 (Macrolin) (for the interleukins);
or a mixture of 1 or 2 inhibitors of inverse transcriptase with 1 or 2 antiproteases (triple therapy).

Other medicaments with no specific anti-HIV purpose are also used to treat opportunist diseases of the infection. For instance, thalidomide, dapsone and certain antibiotics, such as metronidazole or isoniazid can be mentioned.

Thus the invention also has the object of using at least one botulinum neurotoxin to treat or prevent pain caused by medicaments used to treat opportunist diseases of HIV infection, chosen from amongst the following compounds or mixtures of them: thalidomide, dapsone and certain antibiotics such as metronidazole or isoniazid.

Preferably, botulinum neurotoxin makes it possible to achieve a systemic effect.

By "systemic effect", is meant in the sense of the present invention a local administration that makes it possible to obtain a systemic effect.

It is also possible to obtain a local effect if the pain tends to be local.

According to a preferred use of the invention, the botulinum neurotoxin is administered by the subcutaneous, intramuscular or intra-thecal route.

Preferably, the botulinum neurotoxin used according to the invention is chosen from type A, A1, A2, B, C, C1, D, E, F or G botulinum neurotoxins.

Type A1 botulinum neurotoxin corresponds in fact to the conventional botulinum toxin, which is commonly known as type A botulinum toxin, without distinguishing the sub-type. Type A1 botulinum neurotoxin is marketed under the names DYSPORT® and BOTOX®.

According to the invention, type A1 botulinum neurotoxin can correspond either to a complex of botulinum toxin A1 and hemagglutinin, or to botulinum toxin type A1 devoid of any complexing proteins.

Type A2 botulinum toxin was initially isolated from children who contracted botulism around 1990 (Sakaguchi et al., *Int. J. Food Microbiol.* (1990), 11, 231-242).

This toxin is immunologically and biochemically different from type A1 botulinum toxin.

Type A2 botulinum toxin can be isolated from the following strains: Kyoto-F, Chiba-H, Y-8036, 7103-H, 7105-H, KZ1828, NCTC2012 or NCTC9837 (Cordoba et al., *System. Appl. Microbiol.* (1995), 18, 13-22; Franciosa et al., abstract presented at the 40$^{th}$ Interagency Botulism Research Coordinating Committee (IBRCC) Meeting, November 2003).

Preferably the botulinum neurotoxin used according to the invention is botulinum toxin type A1.

According to a variant of the invention, the botulinum neurotoxin used according to the invention is type A2 botulinum toxin isolated from the strain *Clostridium botulinum*, which is referenced and accessible under number NCTC9837 from the National Collection of Type Cultures—Central Public Health Laboratory—London—UK. Strain NCTC9837 is sometimes designated the Mauritius 1955 strain.

Type A2 botulinum toxin differs from the A1 toxin by, amongst other things, its amino acid sequence, its molecular weight and its immunological and genetic characteristics (Kubota et al., *Biochem. Biophys. Res. Commun.* (1996), 224 (3), 843-848).

According to a preferred method, the botulinum neurotoxin used according to the invention is a modified botulinum neurotoxin in which at least one amino acid has been deleted, modified or replaced.

Preferably the botulinum neurotoxin used according to the invention is associated with at least one polysaccharide or a mixture of several polysaccharides.

By polysaccharide, is understood in the meaning of the present invention, a polymer consisting of at least 2 monomers, the monomers being saccharides. This definition includes the disaccharides.

In the context of the invention, the polysaccharides can be ionic and/or non-ionic.

Preferably, the composition contains at least one polysaccharide consisting mainly of glucose units. The term "mainly" signifying that glucose constitutes the numerical majority of the monomer units.

As an example of appropriate polysaccharides according to the use of the invention, we can mention starch, starch derivatives, hydroxyethyl starch and in particular 2-hydroxy-ethyl starch.

Suitable polysaccharides according to the present invention can be substituted, in particular they can be substituted with alkyl, or alkoxy radicals, or with alkyl radicals themselves substituted with alcohol functions.

According to a variant of the invention, the appropriate quantity of polysaccharide according to the present invention is at least 1 μg of polysaccharide for 1 unit of botulinum toxin. Depending on the choice of polysaccharide, it is possible to use at least 0.5 μg of polysaccharide for 1 unit of botulinum toxin.

Preferably the botulinum neurotoxin used according to the invention is associated with at least one surfactant or a mixture of several surfactants.

By a surfactant agent, is signified in the meaning of the invention an emulsifying agent or a solubilizing agent.

In the context of the invention, the surfactants used can be chosen from amongst the cationic, anionic or non-ionic surfactants.

Preferably the botulinum neurotoxin used according to the invention is associated with at least one surfactant or a mixture of several surfactants, chosen from amongst the cationic, anionic or non-ionic surfactants.

Preferably the botulinum neurotoxin used according to the invention is associated with at least one surfactant chosen from amongst the non-ionic surfactants of the polysorbates group.

Amongst the polysorbates group, polysorbate 20, polysorbate 21, polysorbate 40, polysorbate 60, polysorbate 61, polysorbate 65, polysorbate 80, polysorbate 81, polysorbate 85, polysorbate 120, and polysorbate 80 acetate can be mentioned.

The preferred surfactant according to a variant of the invention is polysorbate 80.

The botulinum neurotoxin used according to the invention can be administered preferably by injection, for example by intramuscular, intra-thecal or sub-cutaneous injection.

In the context of injections according to the invention, botulinum neurotoxin can be associated with an agent facilitating the injection also known as the injection vehicle or injection vector.

The dose of the botulinum neurotoxin used according to the present invention required for the treatment or prevention of the diseases or disorders mentioned above, varies depending on the method of administration, age and bodyweight of the subject to be treated and on the state of health of the subject, and it will be decided in the end by the treating physician. This quantity determined in this way by the treating physician is designated here the "therapeutically effective quantity".

Preferably, the botulinum neurotoxin used according to the invention is administered at a dose of between 0.01 U and 1500 U, preferably at a dose of between 0.01 U and 1000 U, more preferably between 0.1 U and 500 U, more particularly at a dose of between 0.1 U and 100 U, still more particularly at a dose of between 1 and 20 U, regardless of the type of botulinum toxin or its origin.

The toxin unit (U) is defined below in the example section.

The object of the present invention is the use of botulinum neurotoxin, described above, to obtain a medicinal product intended for the treatment or prevention of the pain induced by anti-HIV medications, that is the pain linked to a treatment against AIDS.

The abbreviation "AIDS" stands for Acquired immunodeficiency Syndrome. By the expression "AIDS", should be understood in the meaning of the present invention any type of infection by the human immunodeficiency virus, also known as "HIV" in English or "VIH" in French.

Bt the expression "patient suffering from AIDS", is understood in the meaning of the invention both an HIV-positive patient, that is one who has been contaminated by the virus, and a patient who is developing the symptoms of this disease or the opportunist diseases of the infection.

According to the preferred use of the invention botulinum neurotoxin can be used to treat or prevent the pain induced by antiretroviral treatments or the treatments for the opportunist diseases of the HIV infection.

The following example illustrates the invention without limiting its scope.

EXAMPLE

Quantification of the botulinum neurotoxins used according to the invention has been carried out by measuring a lethal dose, the $LD_{50}$. By $LD_{50}$ in the meaning of the present invention is understood the lethal dose or the semi-lethal dose of a given substance.

This is the dose (or quantity) that produces the death of 50% of the animals tested in one group. A toxin unit (U) corresponds to the $LD_{50}$ in mice via the intraperitoneal route.

In example 1, the botulinum toxin used is type A1 botulinum neurotoxin marketed under the proprietary name DYSPORT®.

Example 1

A 31-year-old, HIV-positive male patient receiving treatment for AIDS with a triple therapy with antiretrovirals, presented with severe pain in his left arm, tingling in his arms and legs and burning sensation and hypersensitivity to touch. This hypersensitivity to touch is reflected on his hands by the fact that he cannot put on gloves because he finds this unbearable. These painful symptoms, characteristic of triple therapies, is induced by the triple therapy including antiretrovirals and are side effects of the treatment. The patient is given 3 subcutaneous injections each of 10 U of DYSPORT® in his left arm. After 48 hours the pain completely disappears.

The invention claimed is:

1. A method of treating neuropathic pain in an arm, leg, or hand induced by anti-HIV(Human Immunodeficiency Virus) medicaments in a patient suffering from Acquired Immunodeficiency Syndrome (AIDS) comprising a subcutaneous injection into an arm, leg, or hand of a composition comprising a therapeutically effective amount of botulinum neurotoxin, wherein said administration systemically relieves pain in the arm, leg, or hand not subject to administration.

2. The method of claim 1, wherein the anti-HIV medicament is an inverse transcriptase inhibitor, antiprotease, fusion inhibitor, cytotoxic, interleukin, or mixtures thereof.

3. The method of claim 1, wherein the anti-HIV medicament is zidovudin (AZT), didanosin, stavudin, zalcitabin, lamivudin, neviparin, abacadir, emtricitabin, saquinavir, ritonavir, indinavir, nelfinavir, amprenavir, tenofovir, atazanavir, enfuvirtide, IL2 (Macrolin), or mixtures thereof, or mixture comprising lopinavir, ritonavir, and fosamprenavir.

4. The method of claim 1, wherein the anti-HIV medicament is thalidomide, dapsone, metronidazole, isoniazid, or mixtures thereof.

5. The method of claim 1, wherein the botulinum neurotoxin comprises type A, A1, A2, B, C, C1, D, E, F or G botulinum neurotoxins.

6. The method of claim 1, wherein the botulinum neurotoxin is botulinum neurotoxin type A1.

7. The method of claim 1, wherein the botulinum neurotoxin is associated with at least one polysaccharide or a mixture of several polysaccharides.

8. The method of claim 7, wherein the polysaccharide is 2-hydroxy-ethyl starch.

9. The method of claim 1, wherein the botulinum neurotoxin is a modified botulinum neurotoxin in which at least one amino acid has been deleted, modified or replaced.

10. The method of claim 1, wherein the botulinum neurotoxin is associated with at least one surfactant or a mixture of surfactants comprising cationic, anionic or non-ionic surfactants.

11. The method of claim 1, wherein the botulinum neurotoxin is associated with at least one surfactant comprising non-ionic surfactants of the polysorbate group.

12. The method of claim 1, wherein therapeutically effective amount of a botulinum neurotoxin is between 0.01 U and 1500 U.

13. The method of claim 12, wherein said therapeutically effective amount of a botulinum neurotoxin is at least about 30 U.

14. The method of claim 1, wherein said subcutaneous injection into an arm, leg, or hand comprises 3 subcutaneous injections of 10 U of a botulinum neurotoxin.

15. The method of claim 4, wherein the anti-HIV medicament is dapsone, metronidazole, isoniazid, or mixtures thereof.

* * * * *